(12) United States Patent
Schubert et al.

(10) Patent No.: US 11,471,547 B1
(45) Date of Patent: Oct. 18, 2022

(54) LIGHT FIXTURE WITH ILLUMINATION AND GERMICIDAL LIGHT ENGINES

(71) Applicant: ABL IP Holding LLC, Atlanta, GA (US)

(72) Inventors: John S. Schubert, Arlington Heights, IL (US); Konrad Patryk Pietka, Buffalo Grove, IL (US); Juan A. Rodriguez, Streamwood, IL (US); Christopher Charles Trechter, Chicago, IL (US)

(73) Assignee: ABL IP Holding LLC, Atlanta, GA (US)

( * ) Notice: Subject to any disclaimer, the term of this patent is extended or adjusted under 35 U.S.C. 154(b) by 0 days.

(21) Appl. No.: 17/337,849

(22) Filed: Jun. 3, 2021

(51) Int. Cl.
| | |
|---|---|
| *A61L 2/26* | (2006.01) |
| *F21V 9/40* | (2018.01) |
| *F21V 8/00* | (2006.01) |
| *A61L 2/10* | (2006.01) |
| *F21Y 115/10* | (2016.01) |
| *F21S 8/00* | (2006.01) |
| *F21S 8/02* | (2006.01) |

(52) U.S. Cl.
CPC .............. *A61L 2/26* (2013.01); *A61L 2/10* (2013.01); *F21V 9/40* (2018.02); *G02B 6/0051* (2013.01); *G02B 6/0055* (2013.01); *G02B 6/0088* (2013.01); *A61L 2202/11* (2013.01); *A61L 2202/14* (2013.01); *A61L 2202/25* (2013.01); *F21S 8/026* (2013.01); *F21S 8/036* (2013.01); *F21Y 2115/10* (2016.08)

(58) Field of Classification Search
None
See application file for complete search history.

(56) References Cited

U.S. PATENT DOCUMENTS

| | | | |
|---|---|---|---|
| 8,350,228 B2 | 1/2013 | Welker | |
| 9,439,989 B2 | 9/2016 | Lalicki et al. | |
| 10,101,634 B2 | 10/2018 | Dieudonne et al. | |
| 10,823,369 B2 | 11/2020 | Marry et al. | |
| 2012/0236593 A1* | 9/2012 | Wei | F21S 8/03 362/609 |
| 2022/0016284 A1* | 1/2022 | Portinga | A61L 2/10 |

* cited by examiner

*Primary Examiner* — Britt D Hanley
(74) *Attorney, Agent, or Firm* — Kilpatrick Townsend & Stockton LLP

(57) ABSTRACT

A light fixture includes a visible light module and a germicidal light module. The visible light module may include one or more visible light engines designed for emitting visible light for general illumination. The visible light module may define a top side, a bottom side opposite the top side, and an outer perimeter around the top side and the bottom side. The visible light module may define an aperture extending through the visible light module from the top side to the bottom side. The visible light module may be designed to emit the visible light out of and across the bottom side from the outer perimeter to an inner perimeter defined by the aperture. The germicidal light module may be coupled to the visible light module. The germicidal light module includes a germicidal light engine designed to emit germicidal light through the aperture effective in deactivating pathogens.

22 Claims, 14 Drawing Sheets

LIGHT FIXTURE WITH ILLUMINATION AND GERMICIDAL LIGHT ENGINES

FIELD OF THE INVENTION

The present technology relates to light fixtures including both visible light engines for illuminating an environment and germicidal light engines which may emit germicidal light, for example UV germicidal light engines.

BACKGROUND

Reducing pathogens and improving air quality in indoor spaces occupied by many people, for example office buildings, factories, hospitals, nursing homes and schools, may be important to the health of the occupants. One way of reducing pathogens and improving air quality includes the use of germicidal light. Accordingly, there is a need for adding germicidal lights to indoor spaces.

SUMMARY

The terms "invention," "the invention," "this invention" and "the present invention" used in this patent are intended to refer broadly to all of the subject matter of this patent and the patent claims below. Statements containing these terms should be understood not to limit the subject matter described herein or to limit the meaning or scope of the patent claims below. Embodiments of the invention covered by this patent are defined by the claims below, not this summary. This summary is a high-level overview of various embodiments of the invention and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification of this patent, any or all drawings, and each claim.

In some embodiments, a light fixture includes a visible light module. The visible light module may include one or more visible light engines designed for emitting visible light for general illumination. The visible light module may define a top side, a bottom side opposite the top side, and an outer perimeter around the top side and the bottom side. The visible light module may define an aperture extending through the visible light module from the top side to the bottom side. The visible light module may be designed to emit the visible light out of and across the bottom side from the outer perimeter to an inner perimeter defined by the aperture. In some embodiments, the light fixture may also include a germicidal light module coupled to the visible light module. The germicidal light module may include a germicidal light engine designed to emit germicidal light through the aperture. The germicidal light may be effective in deactivating pathogens.

In some embodiments, the visible light module includes an edge lighting sub-assembly including a light guide. The light guide may define a top surface, a bottom surface opposite the top surface, and a peripheral side between the top surface and the bottom surface. The light guide may define a portion of the aperture between the top surface and the bottom surface of the light guide. The one or more visible light engines may be arranged around the peripheral side in order to emit the visible light into the light guide. The edge lighting sub-assembly may be designed to redirect the visible light entering the light guide from the peripheral side out of the bottom surface so that an intensity of the emitted visible light from the bottom surface is substantially uniform between the peripheral side and the portion of the aperture defined by the light guide.

In some embodiments, the one or more visible light engines include light emitting diodes arranged around the peripheral side of the light guide. In some embodiments, the edge lighting sub-assembly may also include a light blocking sleeve extending through the portion of the aperture defined by the light guide. The light blocking sleeve may define a second aperture. The light blocking sleeve may be designed so that the germicidal light emitted through the aperture is emitted through the second aperture and so that the light guide is not exposed to the emitted germicidal light. The peripheral side may be circular and the portion of the aperture defined by the light guide and the light blocking sleeve may be rectangular. The edge lighting sub-assembly may also include a mounting plate, a reflector plate, and a diffuser plate. The germicidal light module may be coupled to the mounting plate with brackets. The reflector plate may be positioned between the mounting plate and the light guide and may be designed to reflect visible light toward the light guide. The diffuser plate may define the bottom side of the visible light module and may be designed to diffuse the visible light emitted from the bottom surface of the light guide. In some embodiments, the light blocking sleeve may extend through the mounting plate, the reflector plate, the light guide, and the diffuser plate.

In some embodiments, the germicidal light engine may be designed to emit ultraviolet germicidal light effective in deactivating pathogens. The germicidal light engine may be designed to emit a dominant wavelength of 222 nm. The germicidal light engine may include an excimer lamp.

In some embodiments, the germicidal light module includes a dosing circuit module electrically coupled to the germicidal light engine and designed to provide power to and control operation of the germicidal light engine. The dosing circuit module may be designed to not provide power to nor control operation of the one or more visible light engines. The dosing circuit module may be designed to control the germicidal light engine according to a repeating dosing scheme, and the dosing scheme may include a first period between 10 seconds and 2 minutes in duration wherein the germicidal light engine emits the germicidal light followed by a second period between 1 minute and 10 minutes in duration wherein the germicidal light engine does not emit the germicidal light. The germicidal light module may include a status indicator light controlled by the dosing circuit module. The dosing circuit module may be designed to control the status indicator light to provide different indications corresponding to the functionality and remaining service life of the germicidal light engine.

In some embodiments, a light fixture includes a housing, a reflector coupled to the housing, an edge lighting sub-assembly coupled to the housing, and a germicidal light module. The edge lighting sub-assembly may include a mounting plate, a light blocking sleeve, and at least one of a light guide, a reflector plate, and a diffuser plate. The at least one of the light guide, the reflector plate, and the diffuser plate may span across an opening of the reflector. The mounting plate and the least one of the light guide, the reflector plate, and the diffuser plate may define an aperture. The light blocking sleeve may be positioned within the aperture. The germicidal light module may be coupled to mounting plate and include a germicidal light engine designed to emit germicidal light through a second aperture defined by the light blocking sleeve. The germicidal light may be effective in deactivating pathogens.

In some embodiments, the light fixture may also include a visible light module including the edge lighting sub-assembly and a plurality of visible light engines. The edge lighting sub-assembly may include the light guide. The light guide may define a top surface, a bottom surface opposite the top surface, and a peripheral side between the top surface and the bottom surface. The plurality of visible light engines may be arranged around the peripheral side in order to emit visible light into the light guide. The light guide may be designed to redirect the visible light entering the light guide from the peripheral side out of the bottom surface so that an intensity of the emitted visible light from the bottom surface is substantially uniform between the peripheral side and the portion of the aperture defined by the light guide.

In some embodiments, the plurality of visible light engines include light emitting diodes arranged around the peripheral side of the light guide. In some embodiments, the light blocking sleeve is designed so that the light guide is not exposed to the germicidal light emitted through the second aperture. In some embodiment, the peripheral side may be circular and the portion of the aperture defined by the light guide may be rectangular. In some embodiments, the light fixture may or may not include a visible light module including the edge lighting sub-assembly and a plurality of visible light engines. The edge lighting sub-assembly may include the light guide, the reflector plate, and the diffuser plate. The germicidal light module may be coupled to the mounting plate with brackets. The reflector plate may be positioned between the mounting plate and the light guide and may be designed to reflect visible light toward the light guide. The diffuser plate may define a bottom side of the visible light module and may be designed to diffuse the visible light emitted from a bottom surface of the light guide. The light blocking sleeve may extend through the mounting plate, the reflector plate, the light guide, and the diffuser plate. The germicidal light module may include a dosing circuit module electrically coupled to the germicidal light engine and designed to provide power to and control operation of the germicidal light engine. The germicidal light module may include a status indicator light controlled by the dosing circuit module. The status indicator light may be coupled to a shaft of the germicidal light module extending through an opening in the light blocking sleeve. The dosing circuit module may be designed to control the status indicator light to provide different indications corresponding to the functionality and remaining service life of the germicidal light engine.

Various implementations described in the present disclosure can include additional systems, methods, features, and advantages, which cannot necessarily be expressly disclosed herein but will be apparent to one of ordinary skill in the art upon examination of the following detailed description and accompanying drawings. It is intended that all such systems, methods, features, and advantages be included within the present disclosure and protected by the accompanying claims.

BRIEF DESCRIPTION OF THE DRAWINGS

The features and components of the following figures are illustrated to emphasize the general principles of the present disclosure. Corresponding features and components throughout the figures can be designated by matching reference characters for the sake of consistency and clarity.

DETAILED DESCRIPTION

The subject matter of embodiments of the present invention is described here with specificity to meet statutory requirements, but this description is not necessarily intended to limit the scope of the claims. The claimed subject matter may be embodied in other ways, may include different elements or steps, and may be used in conjunction with other existing or future technologies. This description should not be interpreted as implying any particular order or arrangement among or between various steps or elements except when the order of individual steps or arrangement of elements is explicitly described. Directional references such as "up," "down," "top," "left," "right," "front," and "back," among others are intended to refer to the orientation as illustrated and described in the figure (or figures) to which the components and directions are referencing.

The present technology relates to light fixtures including one or more of visible light engines for general illumination of a space with visible light, and germicidal light engines for reducing pathogens and improving indoor air quality. An example of a germicidal light engine includes, but is not limited to, a UV light source.

Figure 1A:
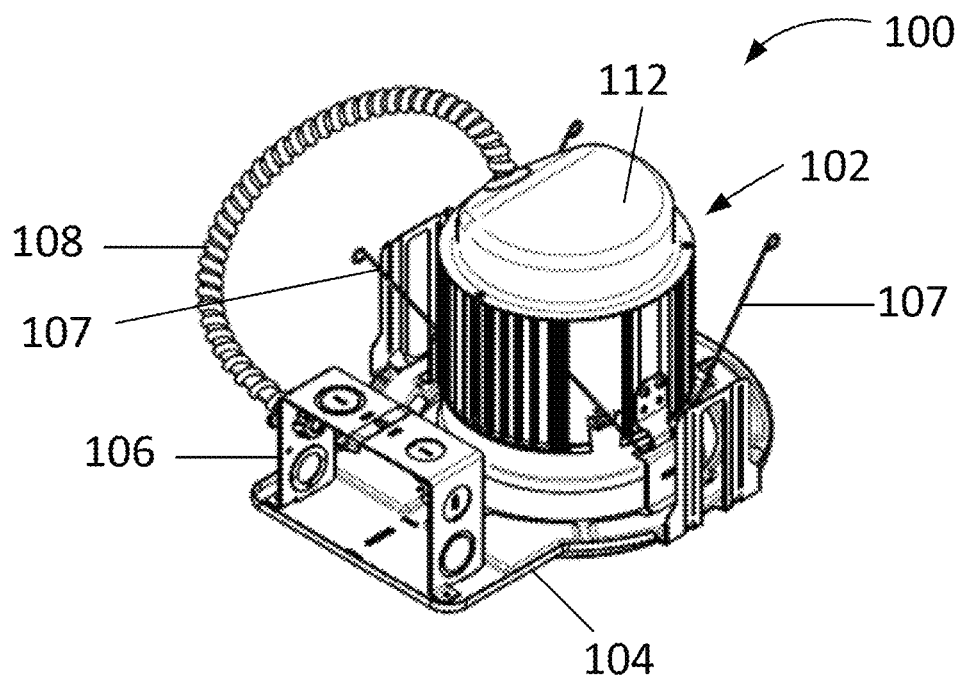
FIGS. 1A-1F show views of a light fixture, according to embodiments of the present technology.
Figure 1B:
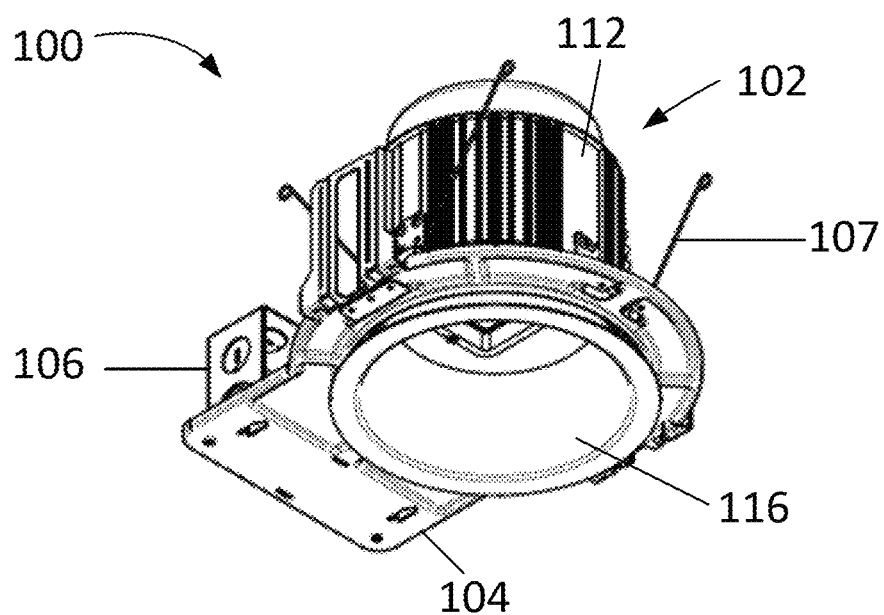
Figure 1C:
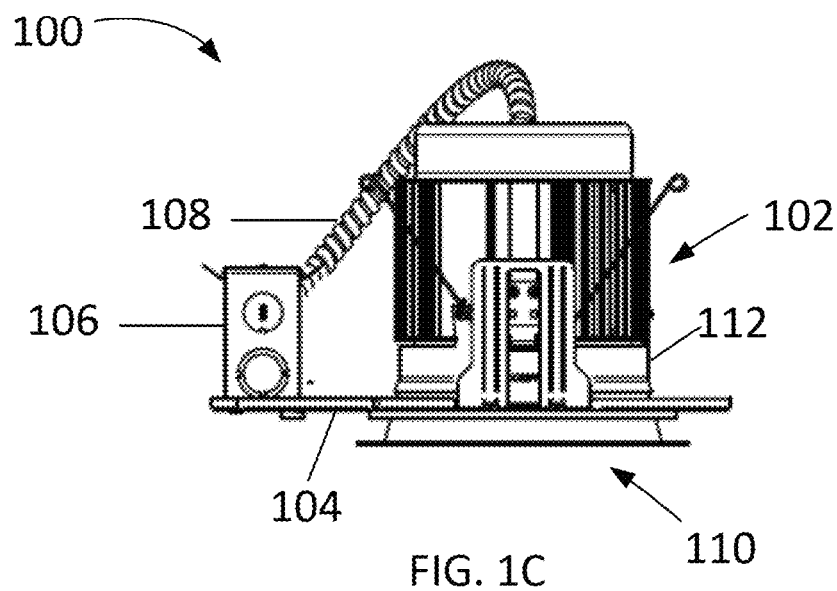

FIGS. 1A and 1B show perspective views of a light fixture 100. As shown, a light fixture 100 may include a light module assembly 102 and mounting hardware for coupling the light module assembly 102 to a building structure, for example a plaster frame 104 for mounting within a ceiling of a building. Light fixtures 100 may further include conduit boxes 106 and conduit 108 extending between the conduit box 106 and the light module assembly 102 for supplying power to electrical components within the light module assembly 102. For example as shown in FIG. 1C, the conduit box 106 may be coupled to the plaster frame 104. As will be discussed in greater detail below, power for visible light components and/or germicidal light components may be provided from the conduit box 106 through the conduit 108 and into the light module assembly 102.

In some embodiments, for example as shown in FIG. 1A-1F, the light fixture 100 may be of a type to be installed in a building within the ceiling with the entire or substantially the entire light fixture 100 positioned within a ceiling. When installed within a ceiling a light-emitting end 110 of the light fixture 100, as indicated in FIG. 1C, is visible from below the ceiling so that light emitted from light engines within the light module assembly 102 illuminate the interior of the building below the light fixture 100.

Figure 8A:
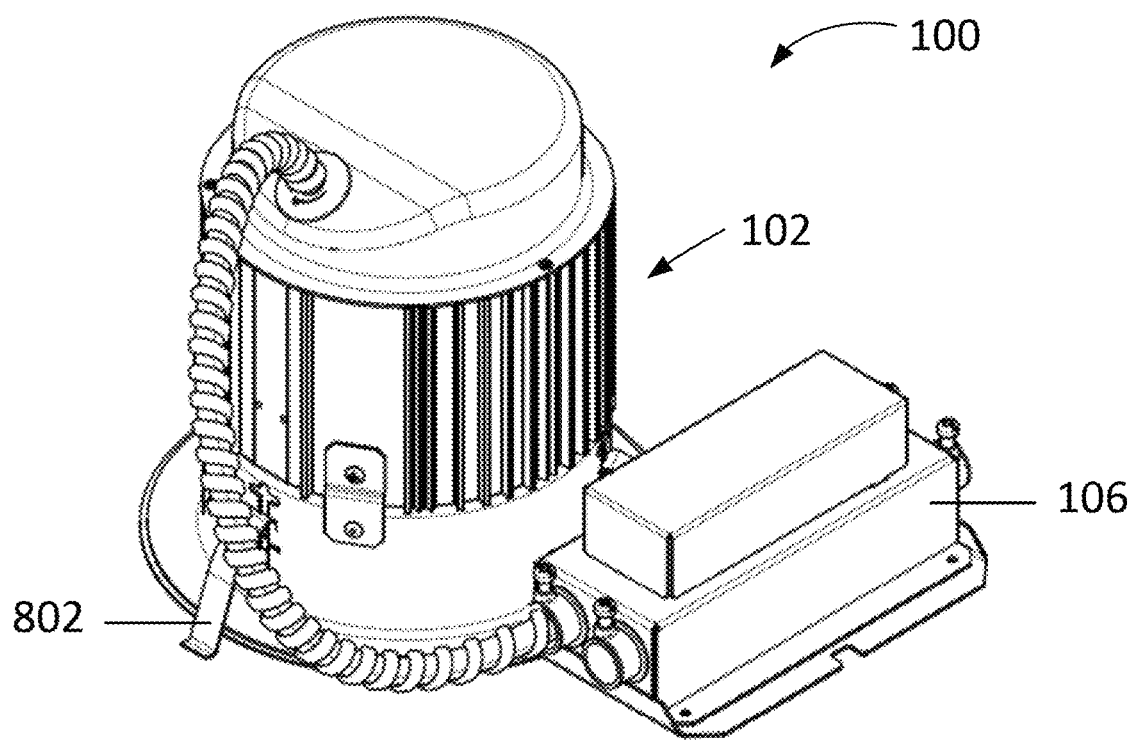
FIGS. 8A and 8B show views of a light fixture, according to embodiments of the present technology.
Figure 8B:
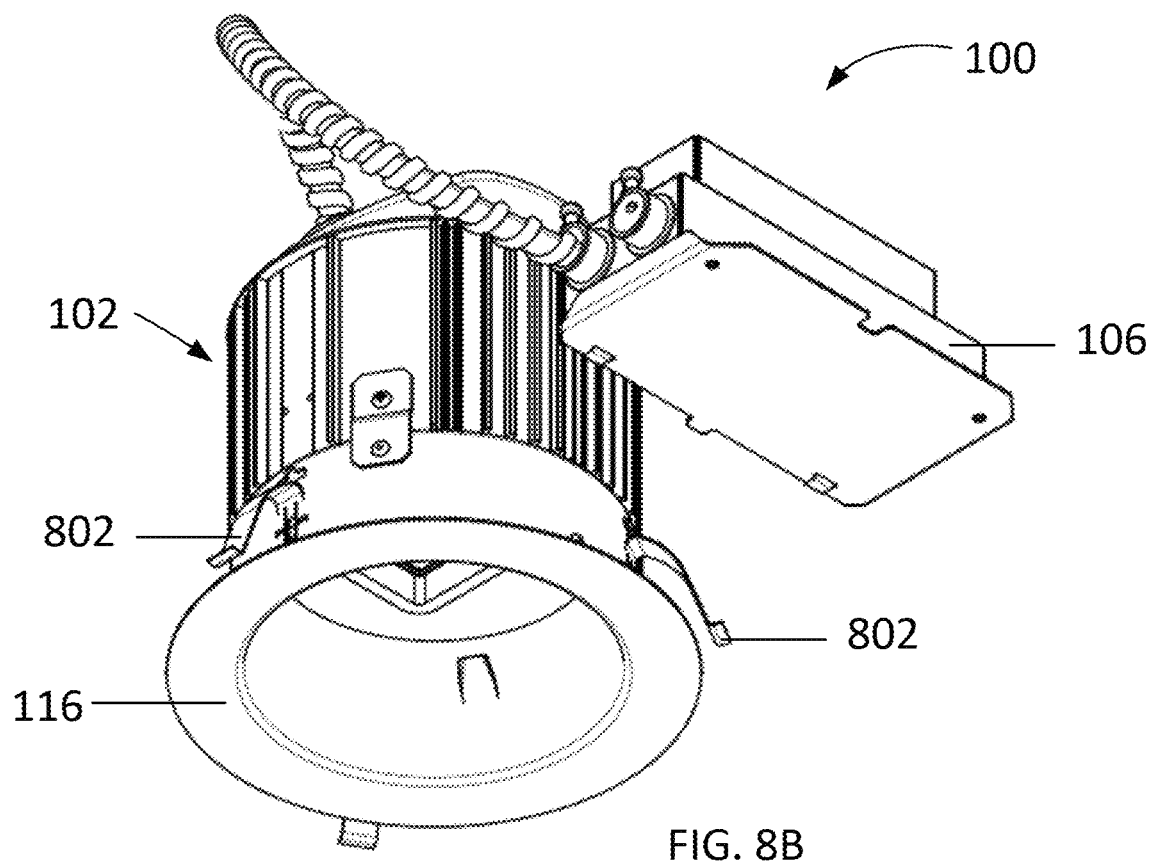
Figure 9A:
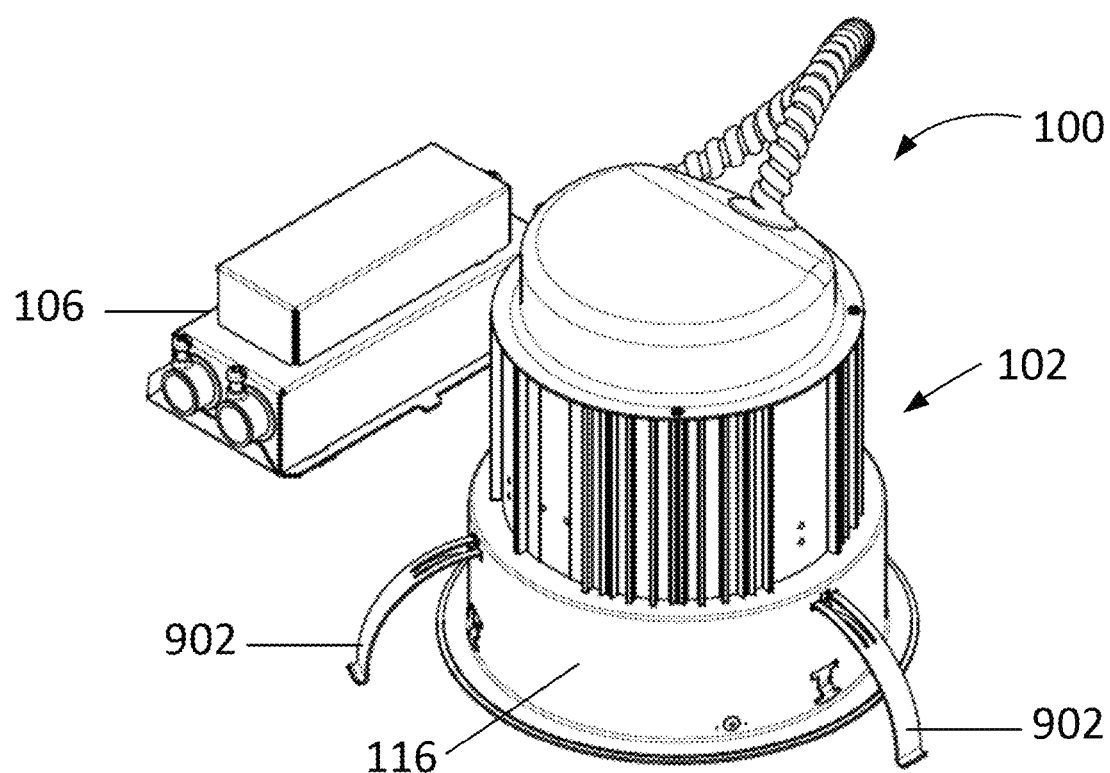
FIGS. 9A and 9B show views of a light fixture, according to embodiments of the present technology.
Figure 9B:
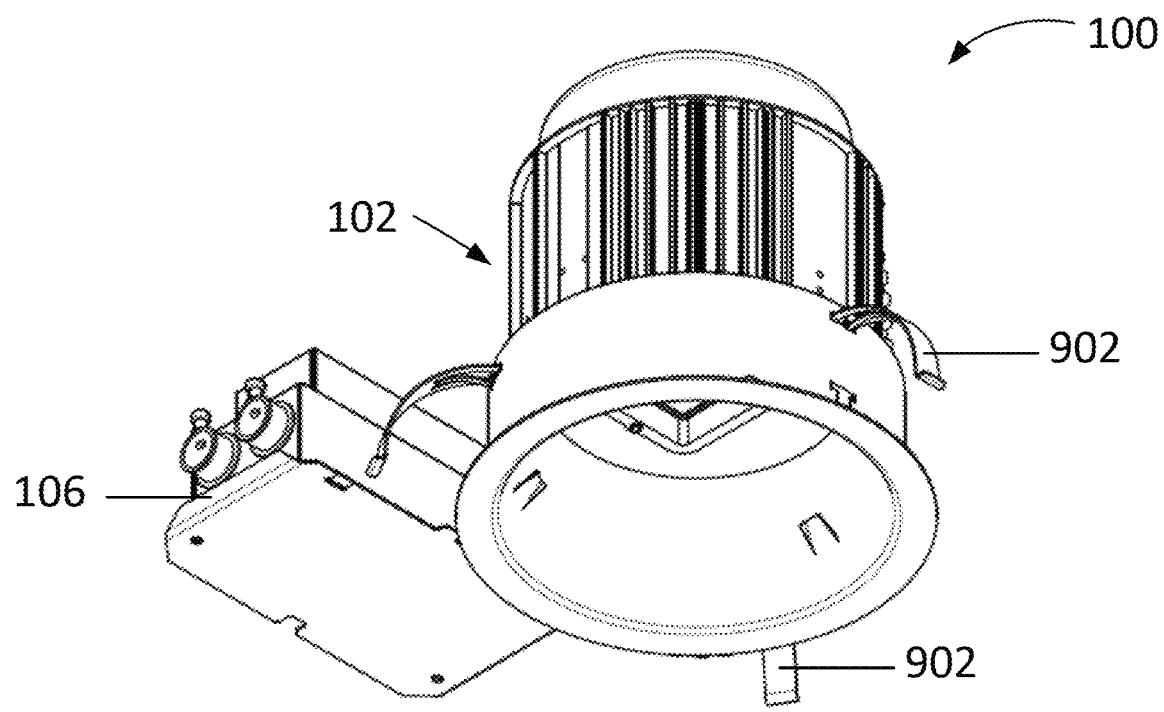
Figures 10A, 10B, 10C:
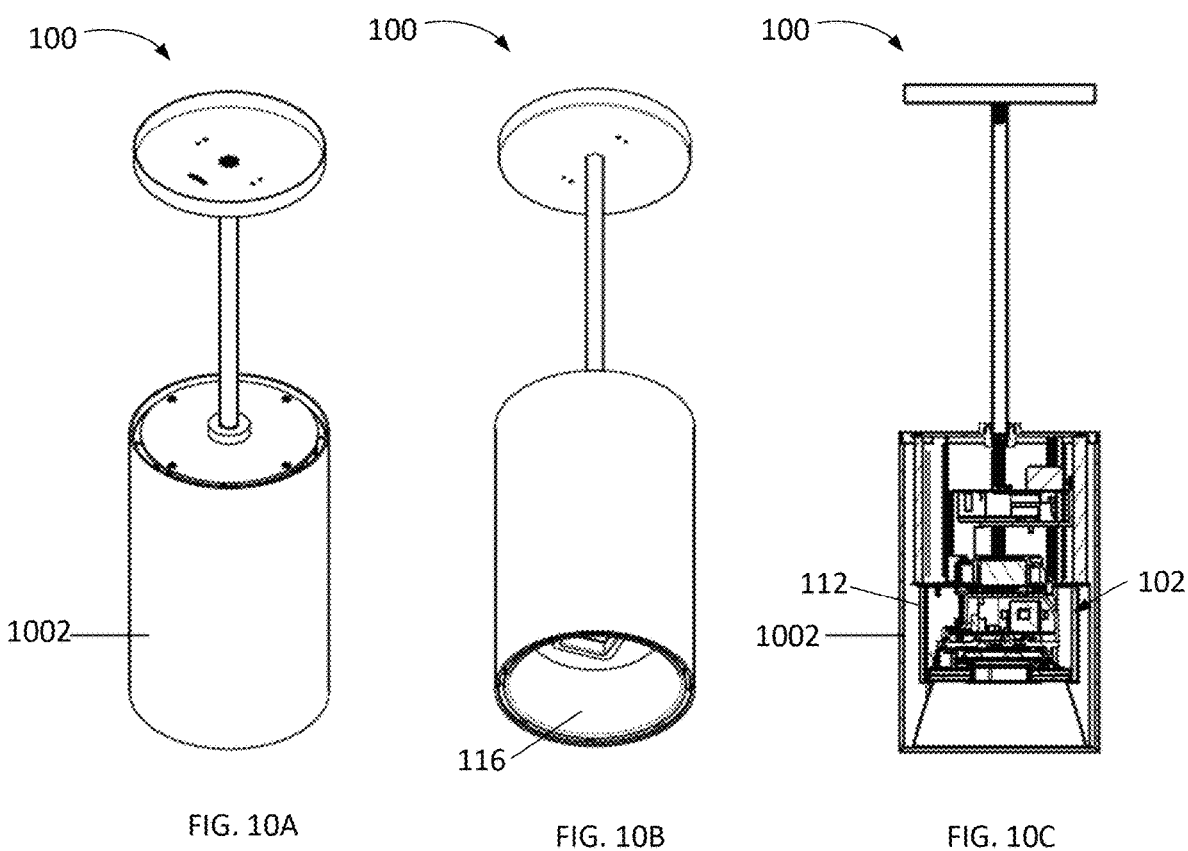
FIGS. 10A-10C show views of a light fixture, according to embodiments of the present technology.
Figure 11A:
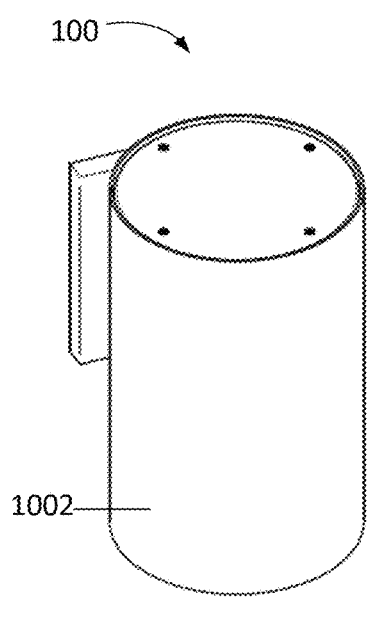
FIGS. 11A and 11C show views of a light fixture, according to embodiments of the present technology.
Figure 11B:
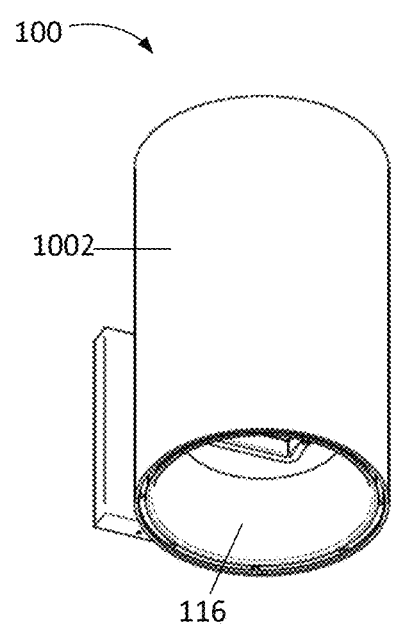
Figure 11C:
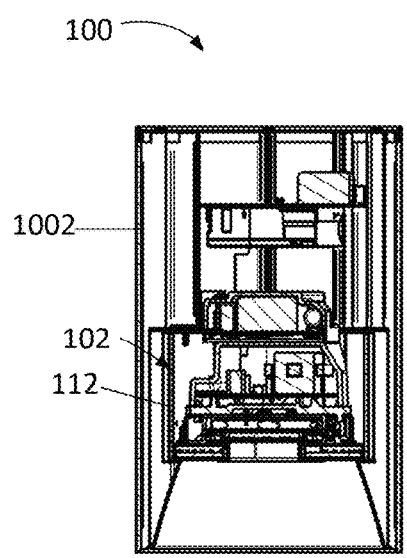

In some embodiments, the light fixture 100 may include mounting hardware for ceiling mounting the light fixture 100 in new construction, for example as shown in FIGS. 1A-1F. In some embodiments, the light fixture 100 may include mounting hardware for retrofitting existing ceiling mounted light fixtures, for example as shown in FIGS. 8A and 8B, wherein mounting hardware in the form of clips 802 are coupled to the light module assembly 102 and are used to retain the light fixture within an already installed plaster frame in the ceiling. In some embodiments, the light fixture 100 may include mounting hardware for remodeling by adding ceiling mountings to an existing ceiling, for example as shown in FIGS. 9A and 9B, wherein mounting hardware in the form of clips 902 are coupled to the light module assembly 102 and are used to retain the light fixture within an opening in the ceiling wallboard. Embodiments for remodeling and retrofitting have the benefit of allowing the addition of germicidal light to existing rooms without substantial modifications to the ceiling. In some embodiments, the light fixture 100 may include an outer housing 1002 in which the light module assembly 102 is positioned within, and the light fixture may be externally ceiling mounted, pendant mounted, for example as shown in FIGS. 10A-10C, or wall mounted, for example as shown in FIGS. 11A-11C.

The light module assembly 102 may include a housing 112 in which the visible light modules 300 and germicidal light modules 700 are mounted. The housing 112 may also house other components, including, but limited to, drivers, batteries, sensors, processors and communication modules (e.g. wired and/or wireless). In some embodiments, for example as shown in FIGS. 1A-1F, the housing 112 is substantially cylindrical. The housing 112 may be extruded from metal, for example aluminum. The housing 112 may include external cooling fins 114, and the components mounted within the housing 112 may be thermally coupled to the housing 112 in order for heat generated by the components to be dissipated by the cooling fins 114. The housing 112 may include internal mounting features coupling the internal light module components to the housing 112. For example, as shown in the cross-sectional view of FIG. 1F, a light module assembly 102 includes: a visible light module 300 and a germicidal light module 700. The visible light module may be coupled to a lower end of the housing 112. The germicidal light module 700 may be coupled to a top side of the visible light module 300. As shown, the light module assembly 102 may further include a reflector 116 coupled to the lower end of the housing 112. The reflector 116 may be coupled with torsion springs 107, as shown in FIGS. 1A and 1B. Visible light emitted from the visible light module 300 may be reflected and focused by an internal surface of the reflector 116.

FIGS. 2A-2D show a light module assembly 102 with the housing 112 omitted to show the internal components mounted within the housing 112. As shown, the germicidal light module 700 is coupled to the visible light module 300 with brackets 202 extending from and coupled to a top surface of the visible light module 300.

The visible light module 300 may be shaped and sized to span across the housing 112. As shown, the visible light module 300 may be shaped as a circular disk in order to be positioned with a circular housing 112. In some embodiments, the germicidal light module 700 defines a height greater than that of the visible light module 300. Due to the height of the germicidal light module 700, it may be beneficial for the visible light module 300 to have a relatively small vertical height in order to reduce the overall height of the light fixture 100 so that the light fixture may fit into ceilings with limited vertical height.

Figure 2A:
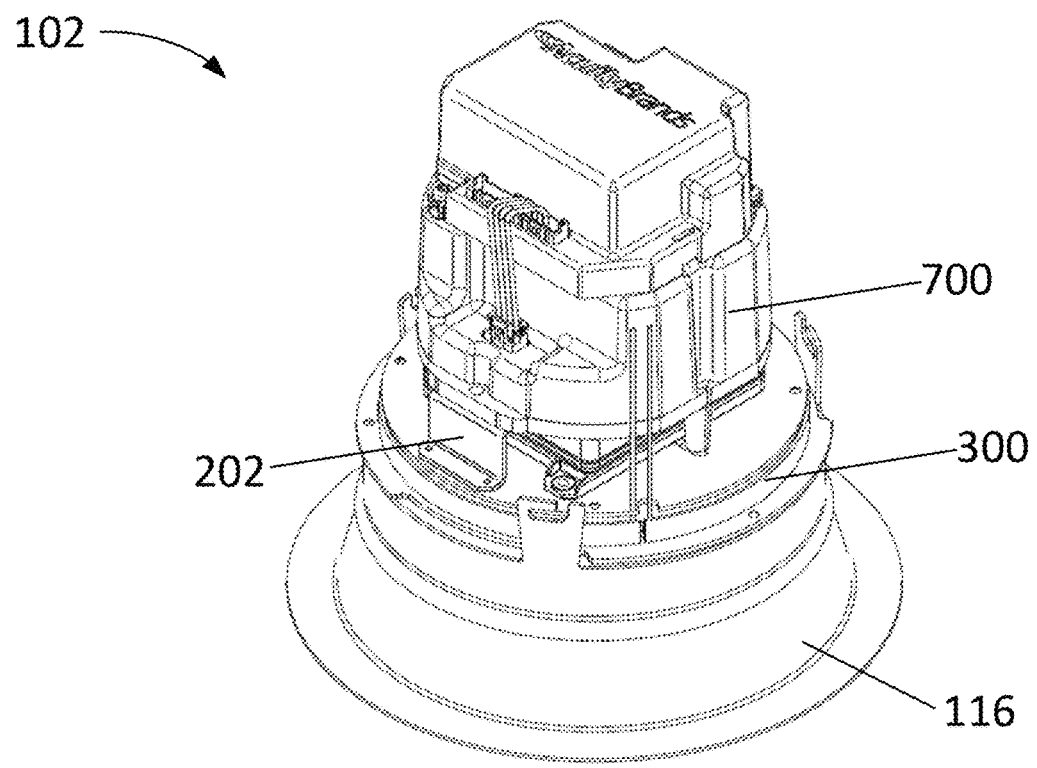
FIGS. 2A-2D show views of an assembly of a visible light module and a germicidal light module, according to embodiments of the present technology.
Figure 2B:
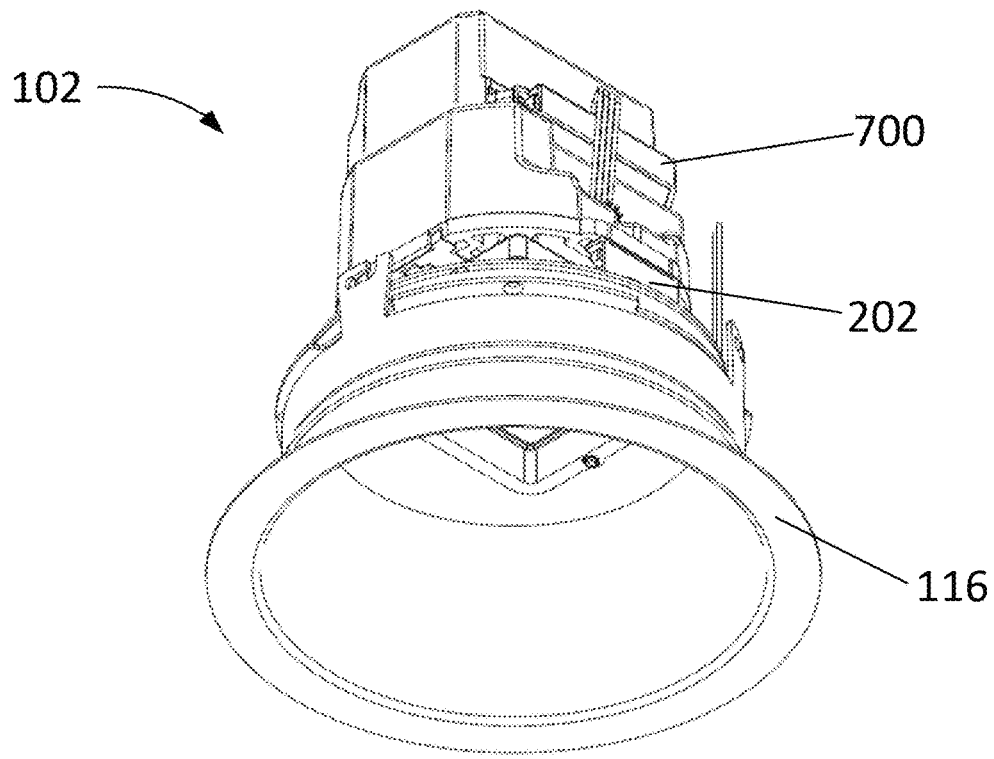
Figure 2C:
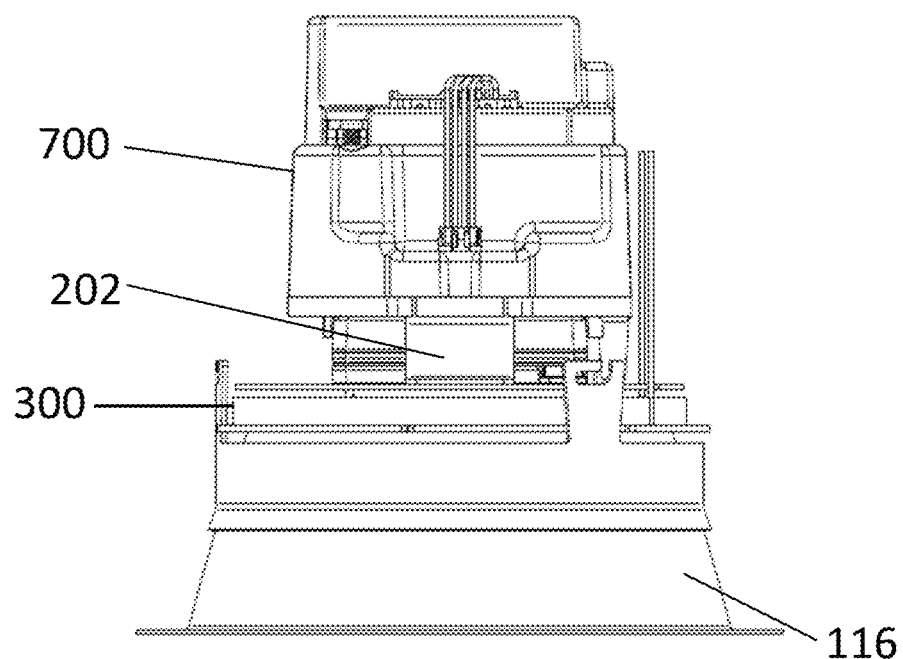
Figure 2D:
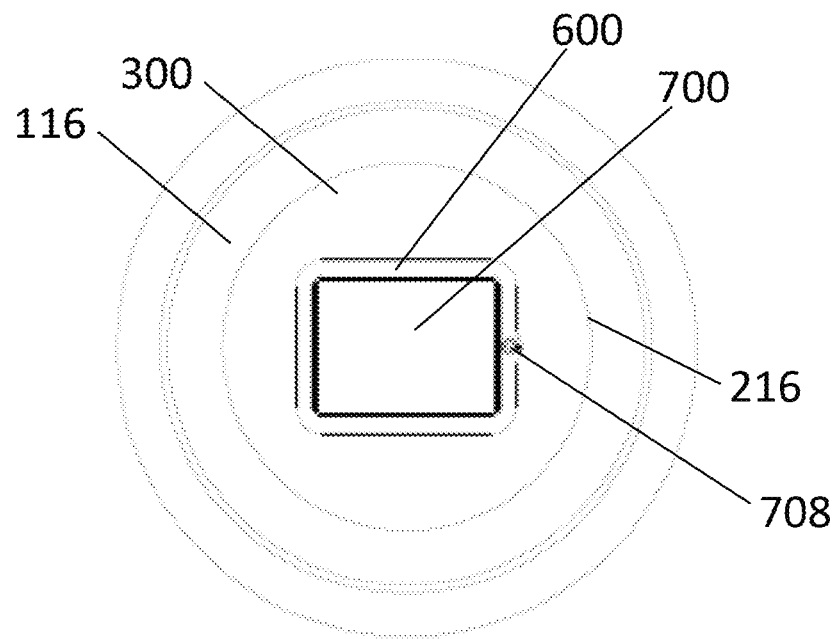

The reflector may be shaped and sized to span across the visible light module 300. As shown in the bottom view of FIG. 2D, the reflector 116 may define a top opening 216 that substantially corresponds in shape and size to a perimeter of the visible light module 300. Further, as shown in FIG. 2D, and as will be discussed in greater detail below, the visible light module 300 includes an aperture through which germicidal light is emitted from the germicidal light module 700, so that both visible light and germicidal light are emitted downward out of the reflector 116. In some embodiments, the germicidal light may be focused so that the germicidal light is not reflected by the reflector 116.

FIGS. 3A-3D show a sub-assembly including the visible light module 300 and the reflector 116. In some embodiments, the visible light module 300 may be directly coupled to the reflector 116, and the reflector 116 may be directly coupled to the housing 112. In some embodiments, the visible light module 300 may be directly coupled to the housing 112, and the reflector may be directly coupled to the housing 112.

Figure 3A:
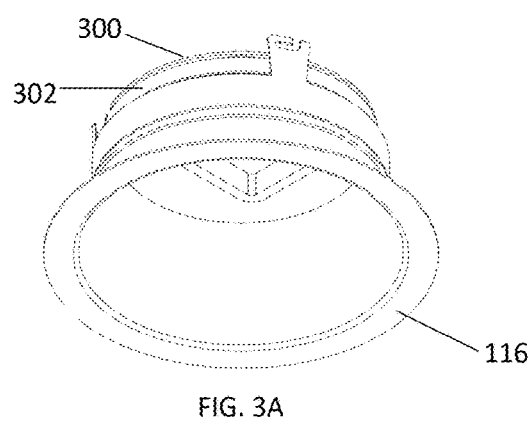
FIGS. 3A-3D show views of a sub-assembly including a visible light module and a reflector, according to embodiments of the present technology.
Figure 3B:
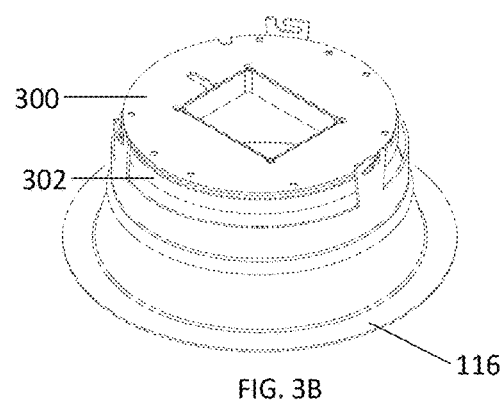
Figure 3C:
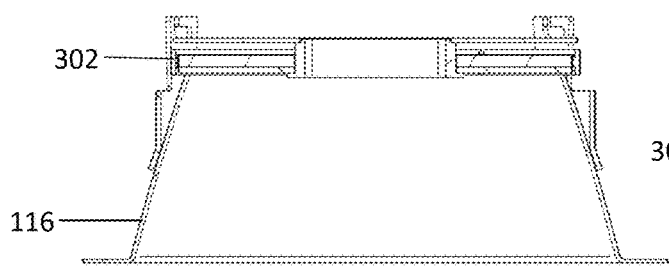
Figure 3D:
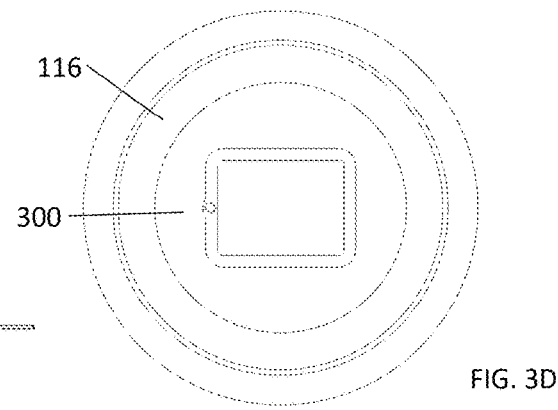

As shown in the cross-sectional view of FIG. 3C, the visible light module 300 may include an outer frame 302 and an edge lighting sub-assembly 400. The outer frame 302 may be circular. As will be discussed in greater detail below, one or more visible light engines 502 may be coupled to an inner face of the outer frame 302 and direct visible light into the edge lighting sub-assembly 400.

Figure 4A:
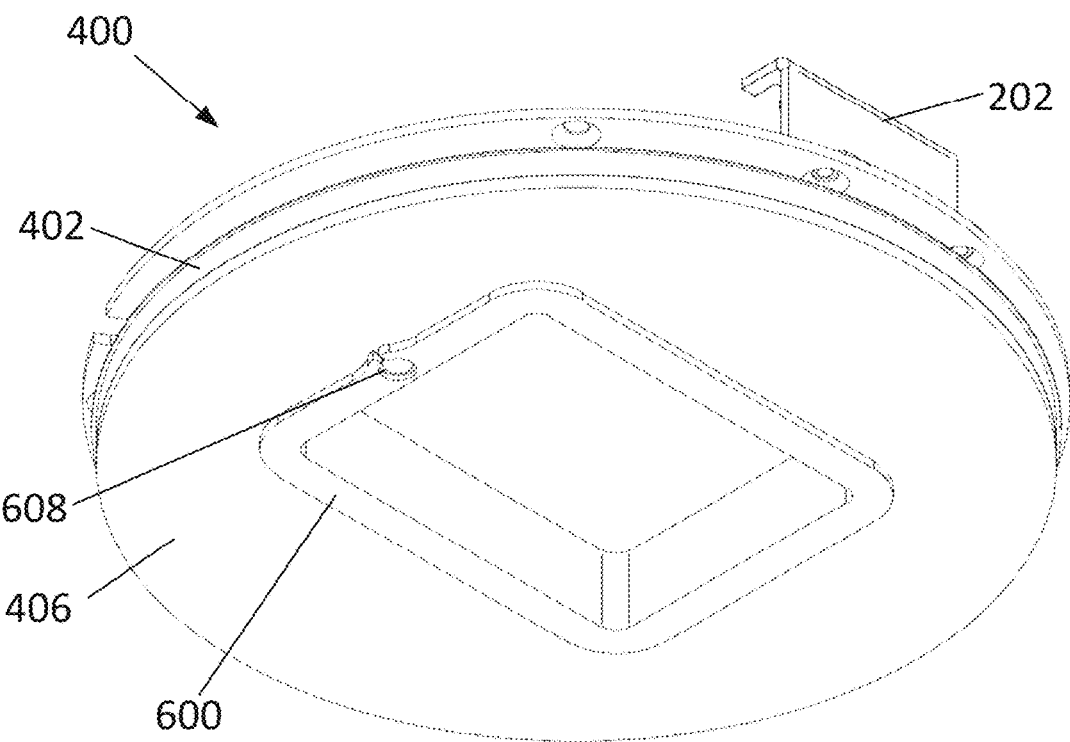
FIGS. 4A and 4B show views of an edge lighting sub-assembly, according to embodiments of the present technology.
Figure 4B:
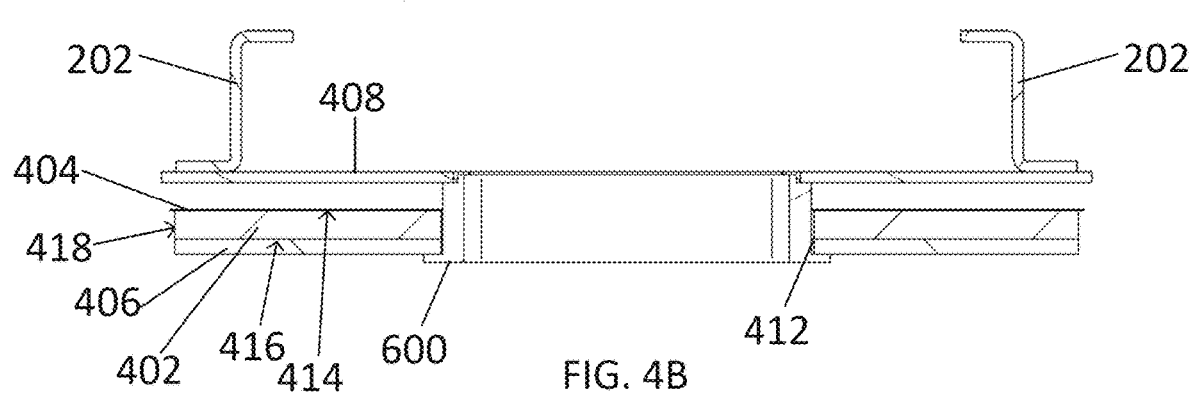

FIGS. 4A and 4B show views of an edge lighting sub-assembly 400. An edge lighting sub-assembly 400 may include a light guide 402, a reflector plate 404, a diffuser plate 406, a mounting plate 408 and a light blocking sleeve 600. The reflector plate 404, light guide 402, diffuser plate 406 and mounting plate 408 have a similar profile shape. For example, as shown in FIGS. 4A and 4B, each of the reflector plate 404, light guide 402, diffuser plate 406 and mounting plate 408 define a circular outer perimeter. Further, each of the reflector plate 404, light guide 402, diffuser plate 406, and mounting plate 408 each define a portion of an aperture 412 for receiving the light blocking sleeve 600. As shown the aperture 412 and correspondingly shaped light blocking sleeve 600 may be substantially rectangular but could be other shapes. The aperture 412 and correspondingly shaped light blocking sleeve 600 may be sized and shaped based on the emitted light pattern of the germicidal light module 700. For example, germicidal light module 700 emitting germicidal light in a rectangular pattern may be used with a substantially rectangular light blocking sleeve 600.

As shown in FIG. 4B, the reflector plate 404, light guide 402, diffuser plate 406, and mounting plate 408 may be arranged in a stacked configuration defining a top side and a bottom side of the visible light module 300. As shown, the light guide 402 is positioned between the reflector plate 404 and the diffuser plate 406, and the mounting plate 408 is arranged over the reflector plate 404. In some embodiments, a foam pad is positioned between the mounting plate 408 and the reflector plate 4040, and the foam pad may exert a force to press the stack of the reflector plate 404, the light guide 402, and diffuser plate 406 away from the mounting plate and toward a flange 604 of the light blocking sleeve 600. In order to limit the vertical height of the edge lighting sub-assembly, the height between the top side and bottom side of the visible light module 300 may be less than 25 mm, and more specifically may be less than 15 mm. In some embodiments, for example as shown in FIG. 4B, the perimeter of the edge lighting sub-assembly 400 may be circular. In some embodiments, the perimeter of the edge lighting sub-assembly 400 may be shaped other than circular, including, but not limited to, square, rectangular, oblong, polygonal, and may correspond in size and shape to the outer frame 302.

The reflector plate 404 includes a reflector surface facing a top surface of the light guide. The reflector plate 404 may be made of metal or plastic, and the reflector surface may include surface treatment or coating in order to be reflective, for example a coating of reflective white paint. In embodiments, the reflector plate 404 may directly contact the top surface of the light guide 402 or may be spaced apart with an air gap. In some embodiments, the reflector plate 404 may be formed integrally with the light guide 402, for example a coating on the top surface of the light guide.

The light guide 402 may be made of a transparent material, for example glass, or polymethylmethacrylate (also referred to as acrylic). The light guide 402 may define a top surface 414, a bottom surface 416, and a peripheral side 418. The top surface 414 and bottom surface 416 may be parallel to each other. The peripheral side 418 extends between the top surface 414 and the bottom surface 416 and allows for light to enter into the light guide 402.

The diffuser plate 406 may be made of a transparent or translucent material. For example, the diffuser plate 406 may be made of polymeric materials, glass, silicone and various other suitable materials for light distribution. The diffuser plate 406 diffuses and/or scatters light emitted from the bottom surface 416 of the light guide 402. In some embodiments, the diffuser plate 406 may be formed integrally with the light guide 402, for example a coating or texturing on the bottom surface 416 of the light guide 402.

Figure 1D:
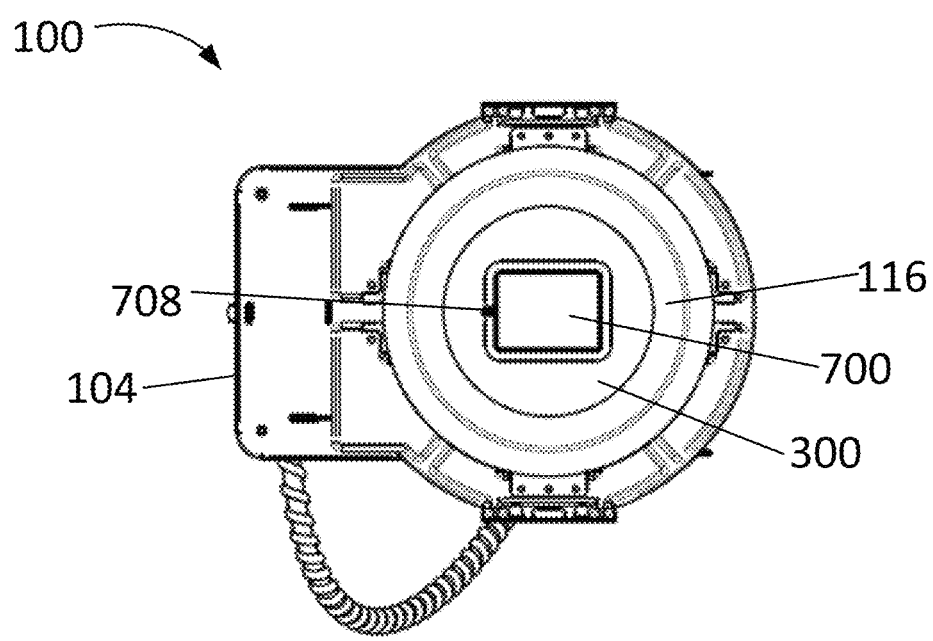
Figure 1E:
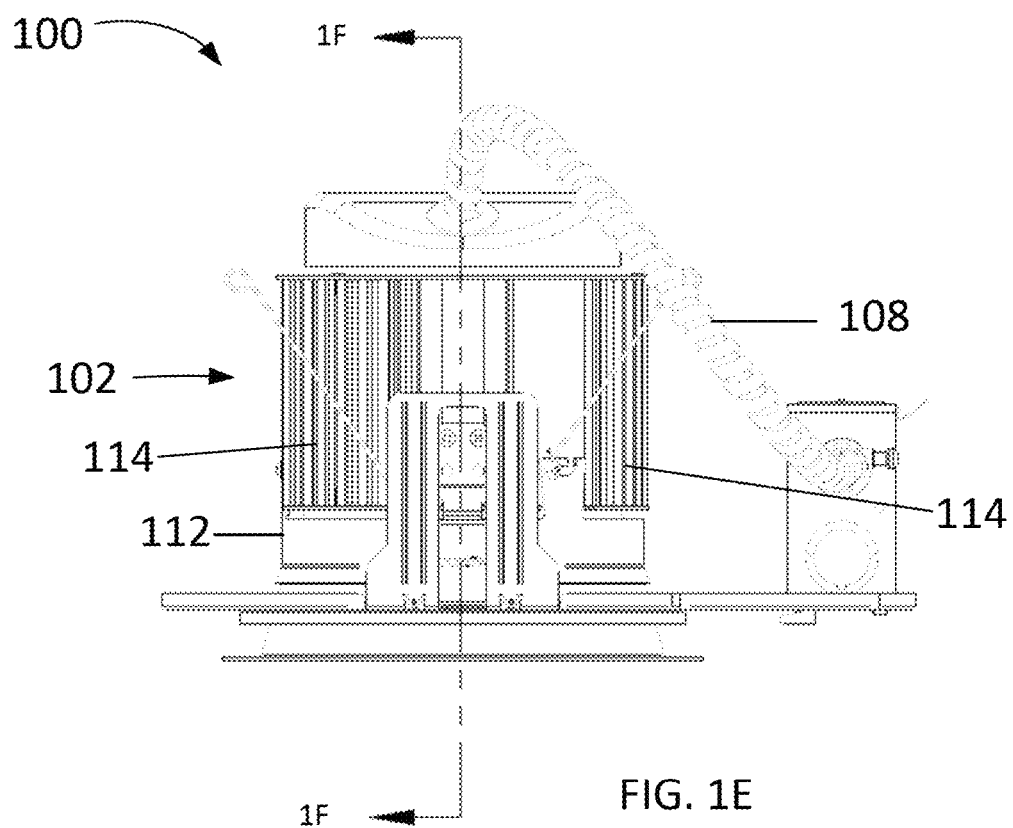
Figure 1F:
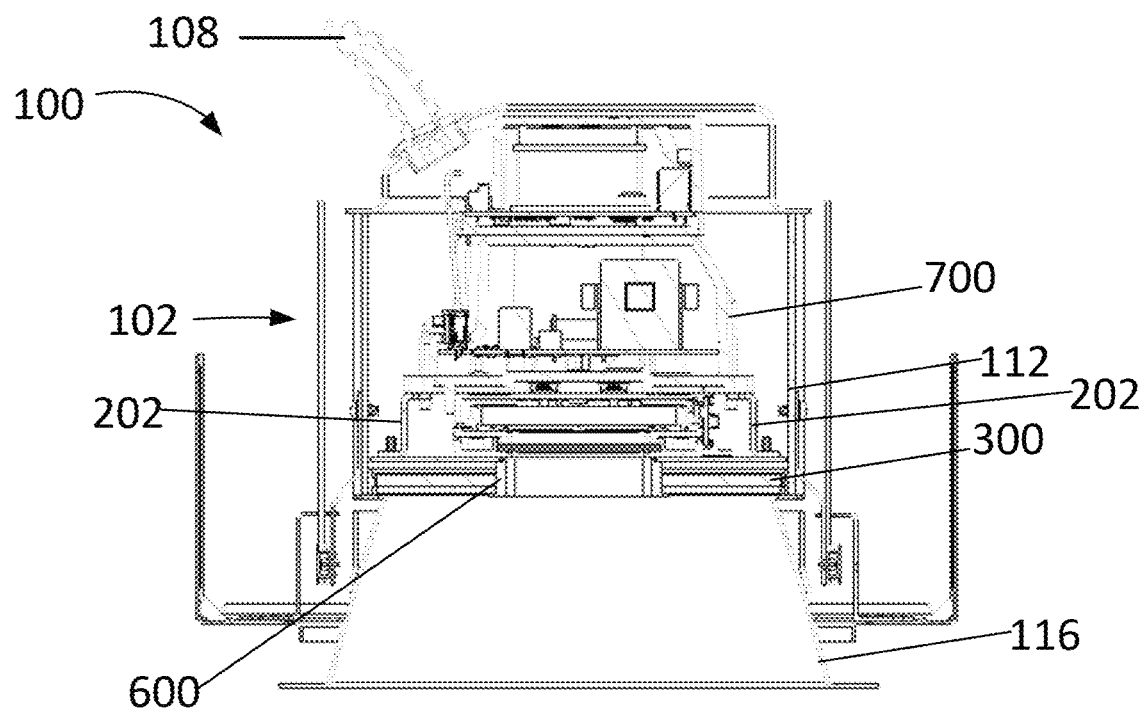

As shown in FIG. 1F, the germicidal light module 700 is mounted via brackets 202 to the mounting plate 408 and is positioned to emit germicidal light through an aperture of the light blocking sleeve 600 of the edge lighting sub-assembly 400. Due to potential material degradation or electrical component damage from interaction between the germicidal light and other components of the system it is beneficial to block germicidal light from reaching unintended components of the light fixture 100. As noted and shown in FIGS. 4A and 4B, the edge lighting sub-assembly 400 includes a light blocking sleeve 600. The light blocking sleeve 600 may be formed of an opaque material, for example metal or plastic. In some embodiments, the light blocking sleeve 600 is formed of aluminum. The germicidal light module 700 may directly contact the light blocking sleeve 600 so that all germicidal light emitted is directed through the aperture of the light blocking sleeve 600 and prevented from passing through the light blocking sleeve 600 due to the opaque material.

Figure 6A:
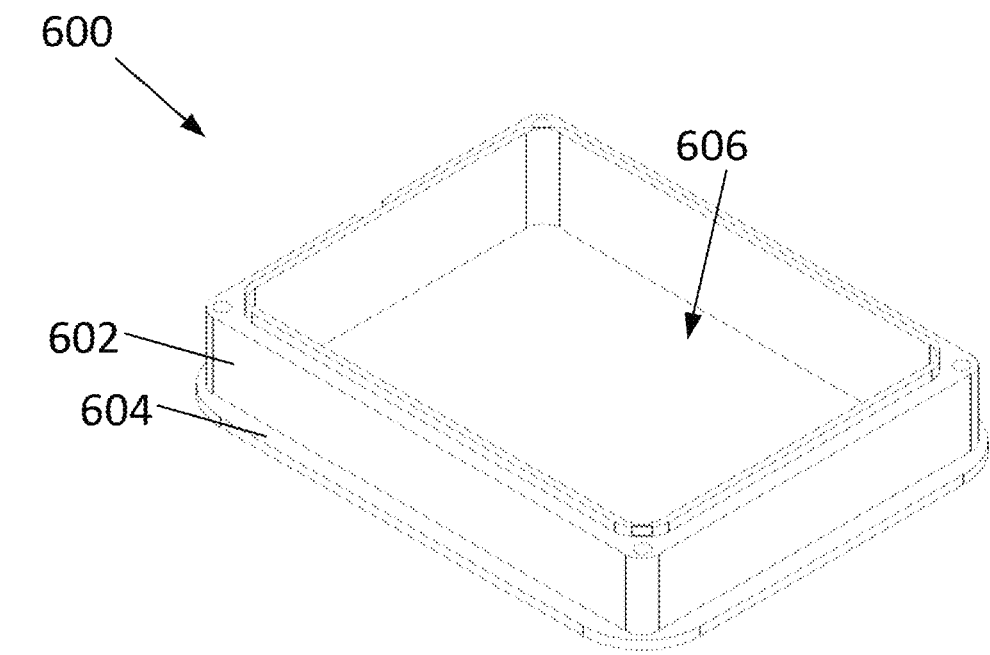
FIGS. 6A-6C show views of a light blocking sleeve, according to embodiments of the present technology.
Figure 6B:
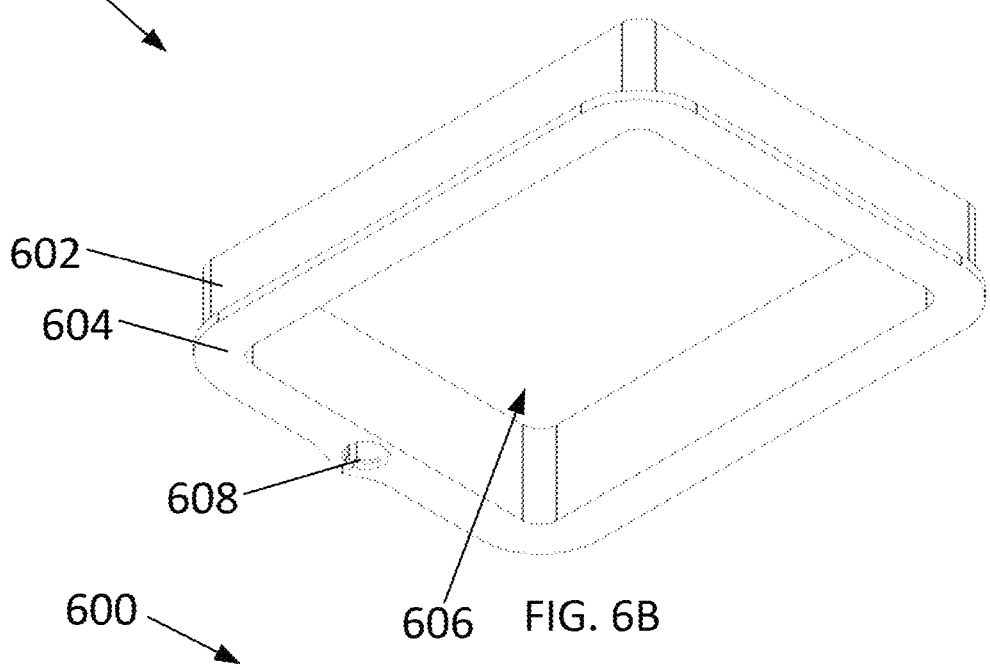
Figure 6C:
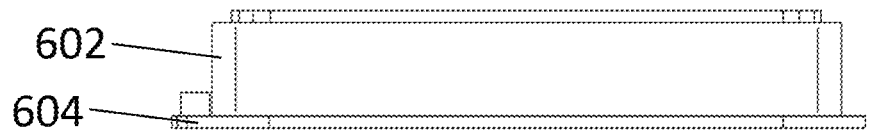
Figure 7A:
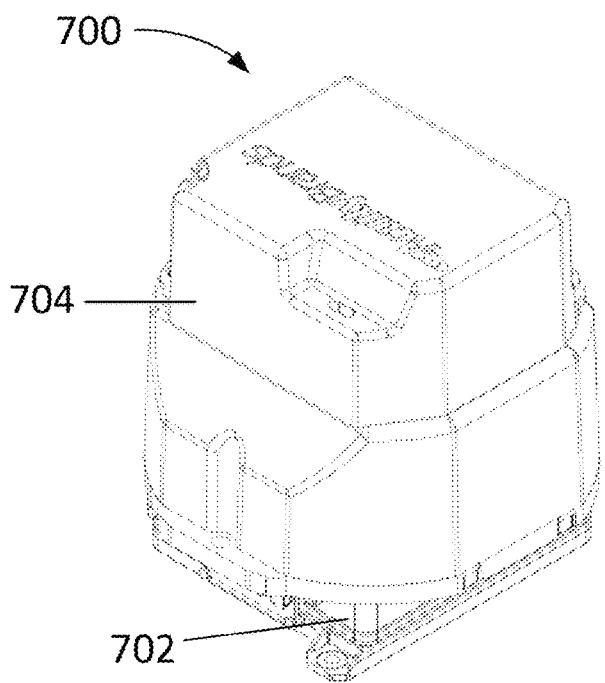
FIGS. 7A-7D shows views of a germicidal lighting module, according to embodiments of the present technology.
Figure 7B:
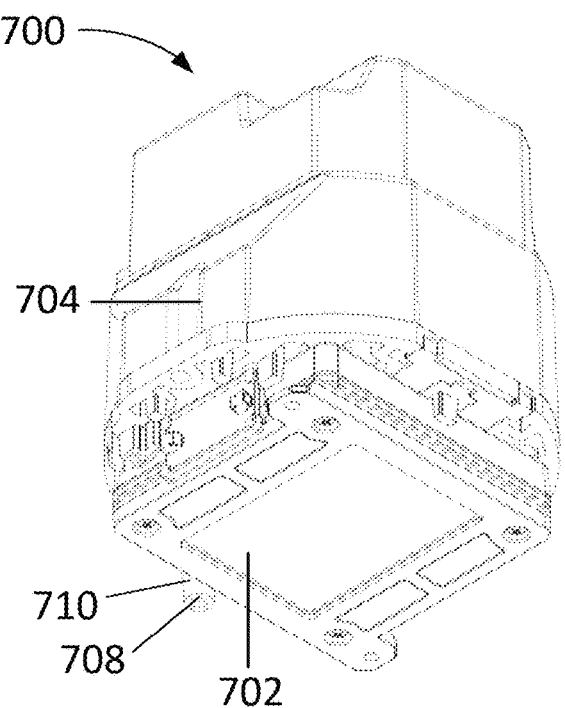
Figure 7C:
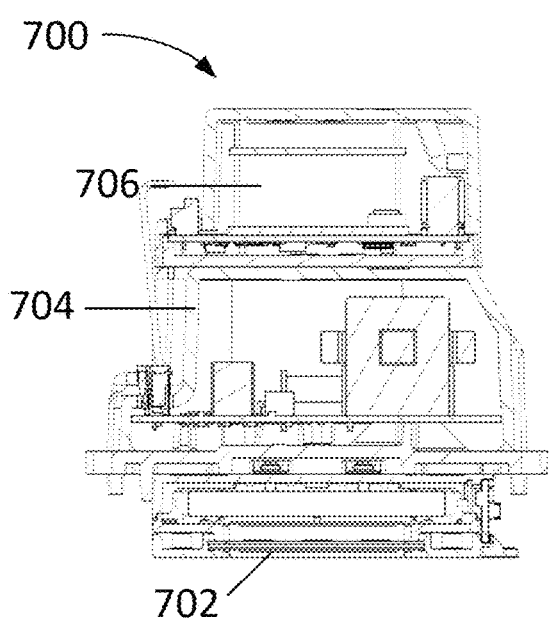
Figure 7D:
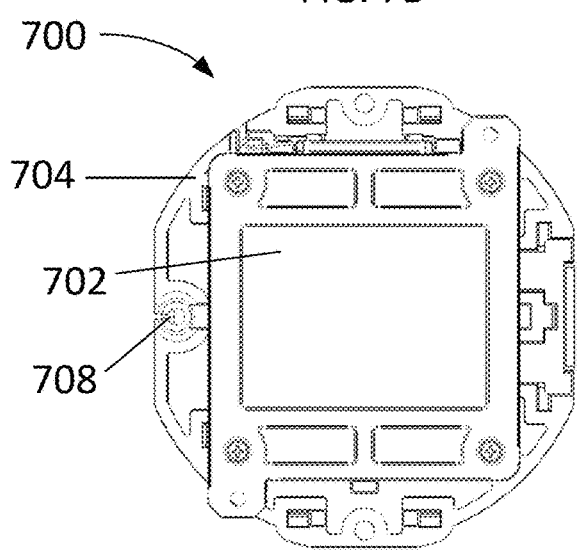

The light blocking sleeve 600, for example as shown in FIGS. 6A-6C, includes a sidewall 602 and a flange 604. The sidewall 602 defines an aperture 606, also referred to as a second aperture, through which germicidal light is emitted from the germicidal light module 700 into a room below the light fixture 100. The sidewall 602 is shaped and sized to be positioned within the aperture 412 defined by the mounting plate 408, the reflector plate 404, the light guide 402, and the diffuser plate 406 with the flange 604 positioned against the diffuser plate 406, so that the sides of the mounting plate 408, the reflector plate 404, the light guide 402 and the diffuser plate 406 defining the aperture 412 are covered by the light blocking sleeve 600. By covering these sides, germicidal light is prevented from reaching, and thus damaging or degrading, other components of the light fixture 100. For example, germicidal light may have a UV wavelength which may degrade the plastic of a light guide 402 and would therefore reduce the diffusing capabilities of the light guide 402 if the light guide were continually exposed to the germicidal light.

Light emitted from one or more visible light engines 502 surrounding the edge lighting sub-assembly 400 enters the light guide 402 from a peripheral side 418. Once within the light guide 402, the light may be diffused through the light guide 402 by reflecting between the top surface 414 and bottom surface 416 of the light guide 402. Light impinging on the top surface 416 may be reflected back into the light guide 402 by the reflector plate 404. Light exiting the light guide 402 through the bottom surface 416 may be additionally diffused through the diffuser plate 406. A combination of one or more of the light guide 402 and the diffuser plate 406 spread the light evenly throughout the edge lighting sub-assembly 400 so that the intensity of the emitted visible light appears to be even between the peripheral side 418 and the light blocking sleeve 600 without bright spots. With this configuration from below the light fixture 100 the entire visible portion of the diffuser plate 406 of the visible light module 300 between the opening of the reflector 116 and the light blocking sleeve 600, as shown in FIG. 2D, emits visible light.

Figure 5A:
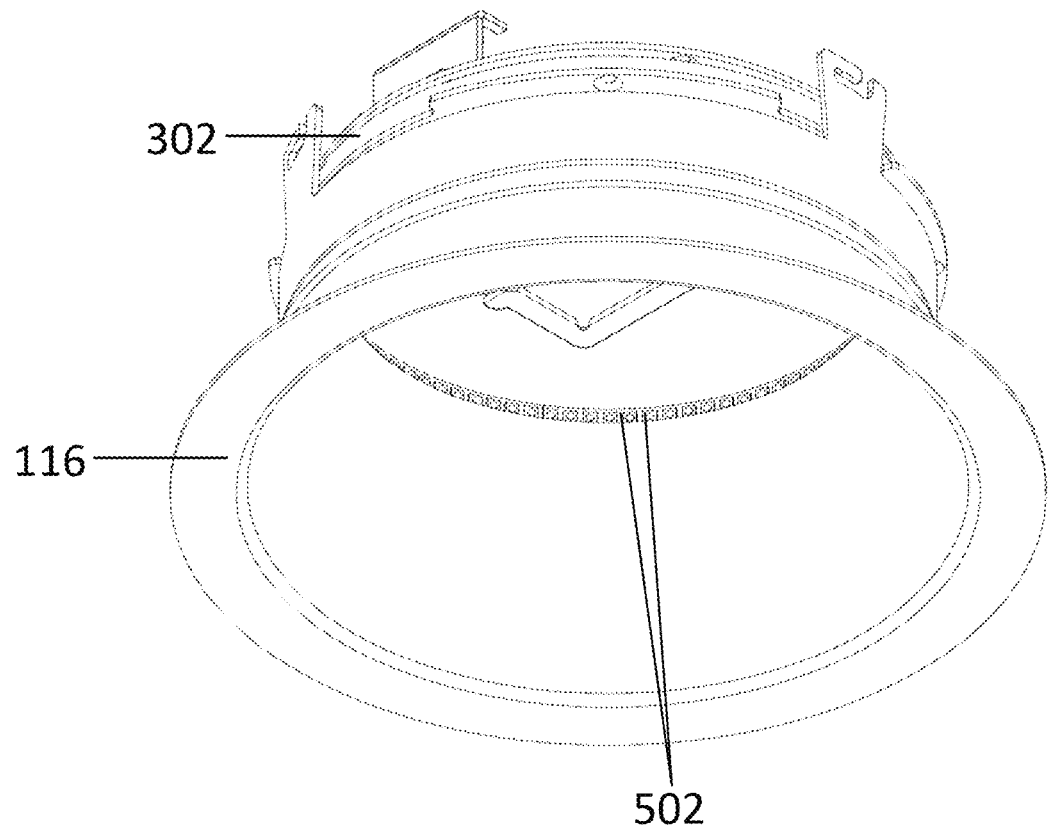
FIGS. 5A and 5B show views of an illumination sub-assembly with components removed to show internal light engines, according to embodiments of the present technology.
Figure 5B:
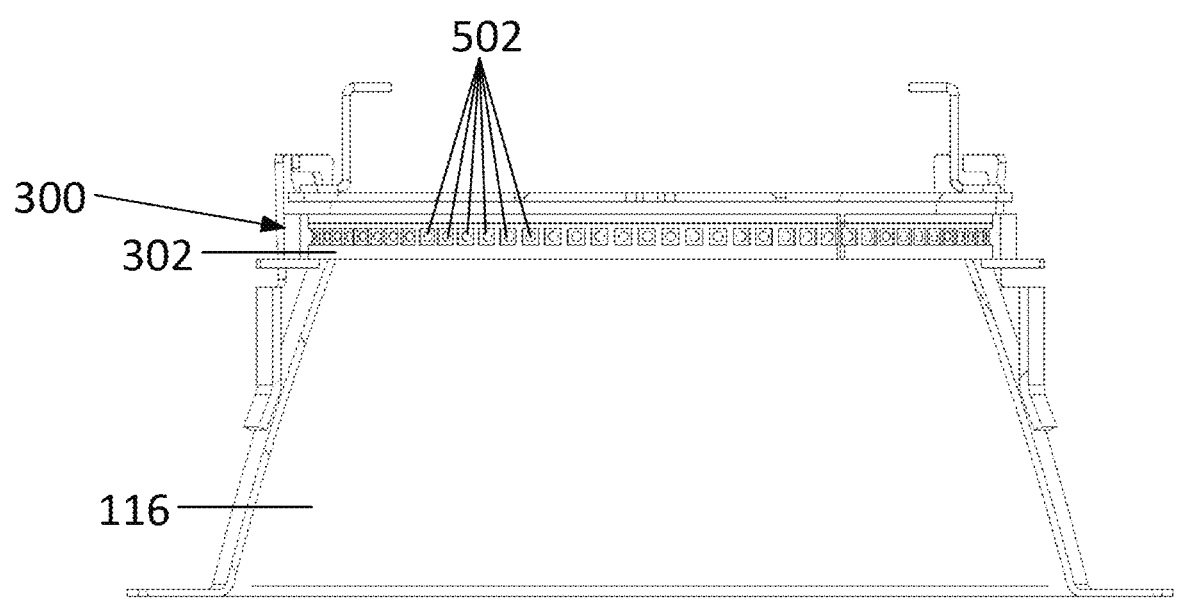

In some embodiments, the one or more visible light engines 502 coupled to the outer frame 302 may be LEDs. FIGS. 5A and 5B show an assembly of the reflector 116 and visible light module 300, with the diffuser plate 406, light guide 402, and reflector plate 404 removed in order to show the visible light engines 502 around the inner periphery of the outer frame 302. For clarity, only a portion of the visible light engines 502 are labeled in the figures. The visible light engines 502 may comprise one or more PCBs populated with LEDs for generating and emitting light, or may be chip-on-board LEDs provided directly on the outer frame 302. In some embodiments, the visible light engine 502 may receive power and/or control signals from one or more visible light drivers. The visible light drivers may be mounted within the housing 112 and/or within the conduit box 106. In some embodiments, the visible light engines 502 may be driverless, for example a driverless LED system. The LEDs may be various types of LEDs including single-die LEDs, multi-die LEDs, direct current (DC) LEDs, alternating current (AC) LEDs, organic light emitting diodes, and/or various other suitable LEDs. White, color, or multicolor LEDs may be used. Moreover, the LEDs need not all be the same color and/or type; rather, mixtures of different colors and/or types of LEDs may be used.

FIGS. 7A-7D show an embodiment of a germicidal light module 700. As shown, the germicidal light module 700 may include a germicidal light engine 702 coupled to a housing 704. In some embodiments, the germicidal light engine 702 may emit visible, IR (invisible), UV (invisible) or a combination of one or more thereof. The germicidal light may be effective in deactivating pathogens. Pathogens include, but are not limited to: micro-organisms, bacteria, viruses, and spores. The germicidal light may deactivate the pathogens, for example, by rupturing the cell membrane or breaking apart a DNA chain or RNA chain in the pathogen.

The frequency spectrum of the germicidal light engine 702 may have dominant wavelengths in the ultraviolet range with wavelengths between 200 nm and 400 nm. The dominant wavelength(s) emitted by the germicidal light engine 702 may be selected in order to deactivate specific pathogen(s) upon exposure to a predetermined dosage. The dominant wavelength(s) may also be selected in order to minimize harmful side effects to humans. In some embodiments, the dominant wavelength of the germicidal light engine is 222 nm, which has been found to deactivate pathogens while also being safe for human exposure. In some embodiments, the germicidal light engine may be an excimer lamp. The excimer lamp may include Xenon monochloride (KrCl) as a working excimer molecule producing a dominant wavelength of 222 nm.

The dosage of the germicidal light may be controlled by the dosing circuit module 706 electrically coupled to the germicidal light engine 702. The dosing circuit module 706 may be included in the germicidal light module 700. The dosing circuit module 706 may define a dosing scheme, also referred to as a disinfecting schedule, wherein the germicidal light engine is turned on to emit germicidal light for a first period followed by a second period wherein the germicidal light engine is turned off. In some embodiments, the first period may be any duration between 10 seconds to 2 minutes, and the second period may be any duration between 1 minute to 20 minutes. For example, the first period may be 20 seconds and the second period may be 12 minutes. The dosing circuit module 706 may run the dosing scheme continuously, i.e. 24 hours a day, so that the germicidal light engine is repeatedly turned on for the first period and turned off during the second period. In some embodiments, the dosing circuit module 706 is run independently from a driver of the visible light engines 502.

The dosing scheme of a dosing circuit module 706 may be selected based on a combination of one or more of: the total number of germicidal light engines in a room, the height of the germicidal light engines above the floor of the room, the duration of exposure needed to deactivate a desired pathogen, and/or the maximum safe dosage for human exposure of the dominant wavelength(s) emitted by the germicidal light engine.

In some embodiments, wherein the germicidal light is invisible, the light fixture 100 may include a visible indicator light 708 for informing an observer of the status of the germicidal light module 700. For example, as shown in FIG. 1D, an indicator light 708 is provided on the flange 604 of the light blocking sleeve 600 so that the indicator light 708 is visible from below the light fixture 100. The indicator light 708 may be positioned at the end of a shaft 710 of the housing 704 of the germicidal light module 700. The shaft may extend through a through hole 608 in a flange 604 of the light blocking sleeve 600, as shown in FIG. 6B.

The indicator light 708 may include an LED, and may be a multi-color LED. The indicator light 708 may be electrically connected to circuitry, for example the dosing circuit module 706, in order to be illuminated to provide the status of the germicidal light engine. For example, the indicator light 708 may be illuminated a first color, e.g. green, to indicate that power is being supplied to the germicidal light engine 702 and that the dosing circuit module 706 is running the dosing scheme. If the indicator light 708 is not illuminated, this may indicate that the germicidal light engine 702 is not receiving power and therefore is not deactivating pathogens. Further for example, the indicator light 408 may be illuminated a second color, e.g. yellow, to indicate that the dosing circuit module 706 has determined that the germicidal light engine 702 is within a predetermined duration of remaining service life, e.g. 1 month of service life left. Further for example, the indicator light 708 may be illuminated a third color, e.g. red, to indicate that the dosing circuit module 706 has determined that the germicidal light engine 702 has reached the end of its service life, and should be replaced as the germicidal light engine 702 may soon no longer emit any light or may have reduced power and no longer be effective in deactivating pathogens.

In some embodiments, the dosing circuit module 706 may be configured to no longer turn on the germicidal light engine 702 when the service life of the germicidal light engine 702 is reached, and may be configured so that a service life duration counter cannot be reset. This configuration is beneficial in ensuring replacement of a germicidal light engine 702 that may no longer be effective in deactivating pathogens.

In some embodiments, the light fixture 100 may be one of a first fixture type that includes both a visible light module 300 including visible light engines and a germicidal light module 700 including a germicidal light engine, a second fixture type that includes only a visible light module 300 including visible light engines, or a third fixture type that includes a germicidal light module 700 with a germicidal light engine but not including visible light engines in a visible light module.

In some embodiments of the second fixture type, a light fixture 100 may include a visible light module 300 that does not include a light blocking sleeve 600 or the corresponding apertures through the diffuser plate 406, light guide 402, and reflector plate 404, so that visible light is evenly distributed throughout the edge lighting sub-assembly 400.

In some embodiments of the third fixture type, a light fixture 100 may include a germicidal light module 700 with a germicidal light engine 702 and a non-functional visible light module 300. In some embodiments, visible light modules 300 that are of the non-functioning type, the edge light sub-assembly 400 may include the mounting bracket 202 and one or more of the diffuser plate 406, the light guide 402, and the reflector plate 404 in order to give the visual appearance of a functional visible light module 300 with the light turned off. Light fixtures with non-functional visible light modules 300 are beneficial in providing a uniform appearance of a plurality of light fixtures 100 in a room without adding unneeded visible light engines. In visible light modules 300 that are of the non-functioning type, the diffuser plate 406, light guide 402, and/or reflector plate 404 may be opaque and colored white or black in order to blend in with other light fixtures in the room which include functional visible light modules 300.

In some embodiments, light fixtures 100 including a germicidal light module 700 with a germicidal light engine 702 and a non-functional visible light module 300 may appear substantially identical to the light fixture shown in FIGS. 1A-1F, and have any of the features disclosed herein pertaining the arrangement of the components.

The light fixtures 100 as disclosed herein may be installed in a room and the light fixtures 100 may include any combination of the three different types of light fixtures in order to achieve a desired number and arrangement of visible light engines and germicidal light engines. The number and types of light fixtures 100 in a room may be selected based on a combination of one or more of, the size of the room, the height of the light fixture mounting location from the floor, and the number available locations for light fixtures.

It will be appreciated that the shape, configuration, and components of the light fixture 100 should not be considered limiting on the present disclosure as the light fixture 100 may have any desired shape or configuration. The above-described aspects are merely possible examples of implementations, merely set forth for a clear understanding of the principles of the present disclosure. Many variations and modifications can be made to the above-described embodiment(s) without departing substantially from the spirit and principles of the present disclosure. All such modifications and variations are intended to be included herein within the scope of the present disclosure, and all possible claims to individual aspects or combinations of elements or steps are intended to be supported by the present disclosure. Moreover, although specific terms are employed herein, as well as in the claims that follow, they are used only in a generic and descriptive sense, and not for the purposes of limiting the described invention, nor the claims that follow.

The invention claimed is:

1. A light fixture comprising:
    a visible light module comprising one or more visible light engines configured to emit visible light for general illumination, wherein the visible light module defines a top side, a bottom side opposite the top side, and an outer perimeter around the top side and the bottom side, wherein the visible light module defines an aperture extending through the visible light module from the top side to the bottom side, and wherein the visible light module is configured to emit the visible light out of and across the bottom side from the outer perimeter to an inner perimeter defined by the aperture; and
    a germicidal light module coupled to the visible light module and comprising a germicidal light engine configured to emit germicidal light through the aperture, wherein the germicidal light is effective in deactivating pathogens.

2. The light fixture of claim 1, wherein the visible light module comprises an edge lighting sub-assembly comprising a light guide,
    wherein the light guide defines a top surface, a bottom surface opposite the top surface, and a peripheral side between the top surface and the bottom surface,
    wherein the light guide defines a portion of the aperture between the top surface and the bottom surface of the light guide,
    wherein the one or more visible light engines are arranged around the peripheral side in order to emit the visible light into the light guide, and
    wherein the edge lighting sub-assembly is configured to redirect the visible light entering the light guide from the peripheral side out of the bottom surface so that an intensity of the emitted visible light from the bottom surface is substantially uniform between the peripheral side and the portion of the aperture defined by the light guide.

3. The light fixture of claim 2, wherein the one or more visible light engines comprise light emitting diodes arranged around the peripheral side of the light guide.

4. The light fixture of claim 2, wherein the edge lighting sub-assembly further comprises a light blocking sleeve extending through the portion of the aperture defined by the light guide,
    wherein the light blocking sleeve defines a second aperture,
    wherein light blocking sleeve is configured so that the germicidal light emitted through the aperture is emitted through the second aperture and so that the light guide is not exposed to the emitted germicidal light.

5. The light fixture of claim 4, wherein the peripheral side is circular and the portion of the aperture defined by the light guide and the light blocking sleeve are rectangular.

6. The light fixture of claim 4, wherein the edge lighting sub-assembly further comprises a mounting plate, a reflector plate, and a diffuser plate,
    wherein the germicidal light module is coupled to the mounting plate with brackets,
    wherein the reflector plate is positioned between the mounting plate and the light guide and is configured to reflect visible light toward the light guide, and
    wherein the diffuser plate defines the bottom side of the visible light module and is configured to diffuse the visible light emitted from the bottom surface of the light guide.

7. The light fixture of claim 6, wherein the light blocking sleeve extends through the mounting plate, the reflector plate, the light guide, and the diffuser plate.

8. The light fixture of claim 1, wherein the germicidal light engine is configured to emit ultraviolet germicidal light effective in deactivating pathogens.

9. The light fixture of claim 8, wherein the germicidal light engine is configured to emit a dominant wavelength of 222 nm.

10. The light fixture of claim 9, wherein the germicidal light engine comprises an excimer lamp.

11. The light fixture of claim 1, wherein the germicidal light module comprises a dosing circuit module electrically coupled to the germicidal light engine and configured to provide power to and control operation of the germicidal light engine.

12. The light fixture of claim 11, wherein the dosing circuit module is not configured to provide power to nor control operation of the one or more visible light engines.

13. The light fixture of claim 11, wherein the dosing circuit module is configured to control the germicidal light engine according to a repeating dosing scheme, and
    wherein the dosing scheme comprises a first period between 10 seconds and 2 minutes in duration wherein the germicidal light engine emits the germicidal light followed by a second period between 1 minute and 10 minutes in duration wherein the germicidal light engine does not emit the germicidal light.

14. The light fixture of claim 11, wherein the germicidal light module comprises a status indicator light controlled by the dosing circuit module, and
    wherein the dosing circuit module is configured to control the status indicator light to provide different indications corresponding to the functionality and remaining service life of the germicidal light engine.

15. A light fixture comprising:
    a housing;
    a reflector coupled to the housing;
    an edge lighting sub-assembly coupled to the housing, wherein the edge lighting sub-assembly comprises a mounting plate, a light blocking sleeve, and at least one of a light guide, a reflector plate, and a diffuser plate, wherein the at least one of the light guide, the reflector plate, and the diffuser plate spans across an opening of the reflector, wherein the mounting plate and the at least one of the light guide, the reflector plate, and the diffuser plate define an aperture, and wherein the light blocking sleeve is positioned within the aperture; and a germicidal light module coupled to mounting plate and comprising a germicidal light engine configured to emit germicidal light through a second aperture defined by the light blocking sleeve, wherein the germicidal light is effective in deactivating pathogens.

16. The light fixture of claim 15, further comprising a visible light module comprising the edge lighting sub-assembly and a plurality of visible light engines,
   wherein the edge lighting sub-assembly comprises the light guide,
   wherein the light guide defines a top surface, a bottom surface opposite the top surface, and a peripheral side between the top surface and the bottom surface,
   wherein the plurality of visible light engines are arranged around the peripheral side in order to emit visible light into the light guide, and
   wherein the light guide is configured to redirect the visible light entering the light guide from the peripheral side out of the bottom surface so that an intensity of the emitted visible light from the bottom surface is substantially uniform between the peripheral side and the aperture defined by the light guide.

17. The light fixture of claim 16, wherein the plurality of visible light engines comprise light emitting diodes arranged around the peripheral side of the light guide.

18. The light fixture of claim 16, wherein the light blocking sleeve is configured so that the light guide is not exposed to the germicidal light emitted through the second aperture.

19. The light fixture of claim 16, wherein the peripheral side is circular and the aperture defined by the light guide is rectangular.

20. The light fixture of claim 15, further comprising a visible light module comprising the edge lighting sub-assembly and a plurality of visible light engines,
   wherein the edge lighting sub-assembly comprises the light guide, the reflector plate, and the diffuser plate,
   wherein the germicidal light module is coupled to the mounting plate with brackets, wherein the reflector plate is positioned between the mounting plate and the light guide and is configured to reflect visible light toward the light guide, and
   wherein the diffuser plate defines a bottom side of the visible light module and is configured to diffuse the visible light emitted from a bottom surface of the light guide.

21. The light fixture of claim 20, wherein the light blocking sleeve extends through the mounting plate, the reflector plate, the light guide, and the diffuser plate.

22. The light fixture of claim 21, wherein the germicidal light module comprises a dosing circuit module electrically coupled to the germicidal light engine and configured to provide power to and control operation of the germicidal light engine,
   wherein the germicidal light module comprises a status indicator light controlled by the dosing circuit module,
   wherein the status indicator light is coupled to a shaft of the germicidal light module extending through an opening in the light blocking sleeve, and
   wherein the dosing circuit module is configured to control the status indicator light to provide different indications corresponding to the functionality and remaining service life of the germicidal light engine.

* * * * *